US010242591B2

(12) United States Patent
King

(10) Patent No.: US 10,242,591 B2
(45) Date of Patent: Mar. 26, 2019

(54) SYSTEM AND METHOD FOR ASSESSMENT OF CARDIOVASCULAR FITNESS

(71) Applicant: The General Hospital Corporation, Boston, MA (US)

(72) Inventor: David King, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 192 days.

(21) Appl. No.: 15/228,494

(22) Filed: Aug. 4, 2016

(65) Prior Publication Data

US 2017/0036065 A1 Feb. 9, 2017

Related U.S. Application Data

(60) Provisional application No. 62/201,040, filed on Aug. 4, 2015.

(51) Int. Cl.
| | |
|---|---|
| *G09B 19/00* | (2006.01) |
| *G06F 19/00* | (2018.01) |
| *G09B 23/28* | (2006.01) |
| *A61B 5/00* | (2006.01) |
| *A61B 5/024* | (2006.01) |
| *A63B 71/06* | (2006.01) |
| *A63B 22/02* | (2006.01) |
| *A63B 22/04* | (2006.01) |

(52) U.S. Cl.
CPC .......... *G09B 19/003* (2013.01); *A61B 5/0022* (2013.01); *A61B 5/02405* (2013.01); *A61B 5/7246* (2013.01); *G06F 19/3481* (2013.01); *G09B 23/28* (2013.01); *A61B 5/7275* (2013.01); *A61B 2503/10* (2013.01); *A63B 22/02* (2013.01); *A63B 22/04* (2013.01); *A63B 71/0622* (2013.01); *A63B 2225/20* (2013.01); *A63B 2225/50* (2013.01); *A63B 2230/04* (2013.01)

(58) Field of Classification Search
CPC .................................................. G09B 19/003
USPC .................................................. 434/255, 247
See application file for complete search history.

*Primary Examiner* — Kesha Frisby
(74) *Attorney, Agent, or Firm* — Quarles & Brady LLP

(57) ABSTRACT

A system and method for assessing cardiovascular fitness of a subject. A local monitoring device is coupled to the subject for acquiring input data related to the subject. A remote monitoring system is communicatively coupled to the local monitoring device over a network for receiving the input data. The remote monitoring system includes a non-transitory memory having stored thereon an algorithm to be applied to the input data. A processor having access to the memory and algorithm is configured to calculate heart rate complexity (HRC) data based on the input data, compare the HRC data to at least one predetermined threshold value, and process the HRC data in relation to the at least one predetermined threshold value to generate a cardiovascular fitness level of the subject. A display is coupled to the remote monitoring system and configured to display a report related to the cardiovascular fitness level of the subject.

14 Claims, 2 Drawing Sheets

SYSTEM AND METHOD FOR ASSESSMENT OF CARDIOVASCULAR FITNESS

CROSS-REFERENCE TO RELATED APPLICATIONS

The present application is based on, claims priority to, and incorporates herein by reference in its entirety, U.S. Provisional Patent Application No. 62/201,040, filed Aug. 4, 2015, and entitled "System and Method for Assessment of Cardiovascular Fitness."

STATEMENT REGARDING FEDERALLY SPONSORED RESEARCH

Not applicable.

BACKGROUND OF THE DISCLOSURE

The present disclosure relates to systems and methods for assessing and tracking cardiovascular fitness. More particularly, the disclosure relates to systems and methods for assessing and tracking cardiovascular fitness using a noninvasive measure of overall cardiovascular fitness and athletic performance.

The field of physical fitness assessment and testing has seen an increasing demand with rising public interest in physical fitness and the relevance of performance to soldiers, firefighters, athletes, and the like. For instance, with the high demand and financial stakes of professional and collegiate athletics, there is strong interest in accurately testing and predicting the physical fitness of the athletes. In addition, the increasingly health-conscious public is interested in assessing physical fitness for personal knowledge. However, conventional vital signs measured by current fitness devices are often inaccurate and poor predictors of cardiovascular fitness in healthy persons.

Thus, health clubs and physiological laboratories now conduct elaborate fitness and performance assessments. Such assessments often test the aerobic and anaerobic fitness of participants. Several different tests have been used to make such aerobic and anaerobic assessments. However, drawbacks of the typical anaerobic and aerobic tests include the length of time and expense involved. For instance, aerobic tests typically require from five to twenty minutes of strenuous exercise. Further drawbacks include the use of sophisticated equipment. Additional drawbacks include, for instance, anaerobic fitness being limited to a power output of a stationary bicycle and not a power output of an individual being tested.

A common laboratory test to predict cardiovascular fitness includes the assessment of maximal oxygen uptake or consumption ($VO_2$max). $VO_2$max is the maximal capacity of an individual to perform aerobic work. $VO_2$max is the product of cardiac output (CO) and arteriovenous oxygen (a-$vO_2$) difference at exhaustion, and the golden standard measure for a person's aerobic fitness. The assessment of a person's $VO_2$max indicates the maximal amount of oxygen the individual can utilize typically over one minute during an intense, maximal physical effort. Aerobic fitness is related to a person's ability to perform dynamic, moderate-to-high intensity physical activity with large muscle groups for prolonged periods. Thus, $VO_2$max expresses the abilities of both cardiorespiratory and muscular systems to transport and utilize oxygen for energy.

Typically $VO_2$max is measured directly by analyzing inspired and expired breathing gases in a laboratory setting during maximal exertion, and expressed either as absolute maximal amount of oxygen per minute (L/min) or as relative to the individual's weight as the maximal milliliters of oxygen the person uses in one minute per kilogram of body weight (ml/kg/min). Individual $VO_2$max values can range from about 10 ml/kg/min in cardiac patients to close to 90 ml/kg/min among world-class endurance athletes. Average values for men and women in different age groups have been used to establish reference fitness categories, as aerobic fitness generally declines with age.

However, as described above, measuring a person's $VO_2$max must be done in a laboratory setting. In addition, laboratory tests require expensive equipment and trained personnel, and are thus difficult and expensive to perform. Therefore, these tests are not feasible for large-scale use and do not allow for frequent follow-up of aerobic fitness.

Thus, it would be beneficial to have systems and methods to measure accurate, real-time cardiovascular fitness information from individuals, without the need for a laboratory setting. Accurate and readily available information could be used, for example, to assess the current fitness level in different populations, motivating towards physical activity, giving feedback on specific exercise sessions or long-term progress, helping to choose suitable exercise modes, and even in planning entire training programs.

SUMMARY OF THE DISCLOSURE

The present disclosure overcomes the aforementioned drawbacks by providing a noninvasive measure overall cardiovascular fitness and athletic performance of an individual using Sample Entropy (SampEn). The present disclosure recognizes that of heart rate complexity (HRC) to determine overall fitness and predict athletic performance with sufficient accuracy and precision that it can be used to predict, for example, marathon qualifying finish times. Additionally, the present disclosure provides a system that utilizes metrics, for example, including left ventricular ejection time and thoracic fluid content, for tracking overall athletic progress.

In one aspect of the present disclosure, a system for tracking athletic fitness of an individual is disclosed. The system includes a sensor configured to be coupled to the individual to acquire cardiac information about the cardiac performance of the individual over time. The system further includes a processor configured to receive the cardiac information from the sensor. The processor is configured to determine, from the cardiac information, a measure of heart function that includes heart rate complexity. The processor is also configured to compare the measure of heart function for the individual to a reference dataset that includes correlated information for a range of individuals of different, known fitness levels to determine a measure of fitness of the individual. A display is coupled to the processor and configured to display the measure of fitness for the individual.

In another aspect of the present disclosure, a system for assessing cardiovascular fitness of a subject is disclosed. The system includes a local monitoring device coupled to the subject for acquiring input data related to the subject. The system further includes a remote monitoring system communicatively coupled to the local monitoring device for receiving the input data. The remote monitoring system includes a non-transitory memory having stored thereon an algorithm to be applied to the input data. A processor has access to the non-transitory memory and the algorithm stored thereon, and the processor is configured to calculate heart rate complexity data based on the input data, compare the heart rate complexity data to at least one predetermined threshold value, and process the heart rate complexity data in relation to the at least one predetermined threshold value to generate a cardiovascular fitness level of the subject. A display is coupled to the remote monitoring system and configured to display a report related to the cardiovascular fitness level of the subject.

In another aspect of the present disclosure a method for assessing cardiovascular fitness of a subject is disclosed. The method includes receiving, from a local monitoring device coupled to the subject, input data related to the subject. Heart rate complexity data is calculated based on the received input data using an algorithm applied to the input data. The heart rate complexity data is compared to at least one predetermined threshold value and processed in relation to the at least one predetermined threshold value to generate a cardiovascular fitness level of the subject. A report related to the cardiovascular fitness level of the subject is generated and displayed on a display communicatively coupled to the local monitoring device.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE DISCLOSURE

Figure 1:
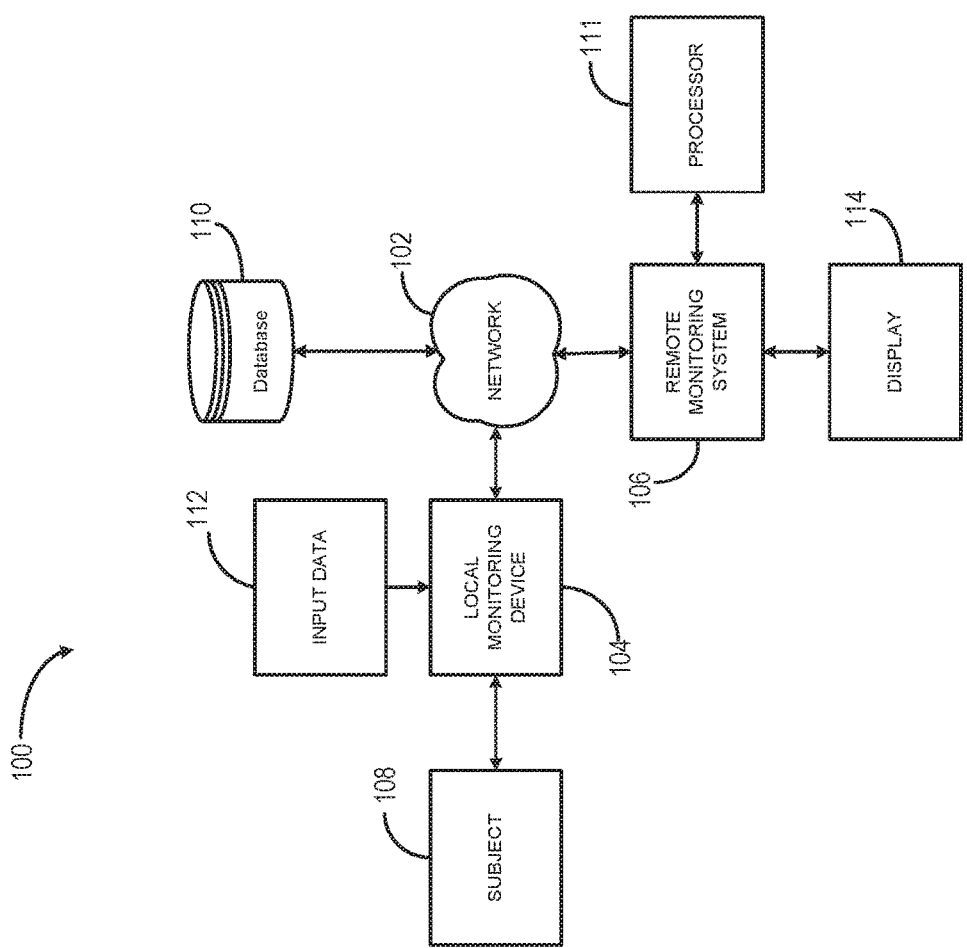
FIG. 1 is a schematic view of an environment in which an embodiment of the disclosure may operate.

Heart rate complexity (HRC) may be a more accurate predictor of cardiovascular health than conventional vital signs, such as blood pressure or heart rate. HRC may represent the body's innate ability to adapt to physiologic stressors. As such, higher HRC may indicate increased cardiac responsiveness to neuroendocrine and autonomic signals, suggesting improved cardiovascular fitness. HRC has shown some utility in the evaluating and triaging trauma patients. Typically, decreased HRC upon hospital arrival is associated with higher rates of mortality, longer hospital stays, and a need for lifesaving interventions. Though many studies have described utility of HRC in the context of disease and trauma, the relevance of HRC in healthy individuals is less known.

HRC is a method of quantifying the amount of complex variability or irregularity in the heart-rate time series. HRC is most often obtained by analyzing R-to-R interval (RRI) of 800 beats or more from a patient's electrocardiogram (EKG). Because generation of HRC can be performed remotely and noninvasively and requires small sections of commonly monitored waveforms, HRC can be integrated into a cardiovascular fitness tool, for example, or prediction of cardiovascular fitness.

As previously described, predictions of cardiovascular endurance capability may be inaccurate without utilizing tests of exertion, such as treadmill or step tests. Furthermore, conventional vital signs such as heart rate may not be sufficient indicators of cardiovascular fitness. In the absence of these specific stress tests, complexity of the normal sinus rhythm may be an indicator of cardiovascular fitness. Increased heart rate variability (HRV) is associated with stronger athletic performance in cyclists, swimmers, and runners, and HRV monitoring may have a role in athletic training regimens. Unlike HRV, which is measured by R-to-R interval variability, HRC quantifies the complexity or irregularity of the EKG signal using nonlinear dynamics. Since biological systems are inherently complex, the nonlinear approach of HRC may have more value in a clinical setting.

Currently, HRV analysis has become an important tool in cardiology because its measurements are noninvasive, easy to perform, have relatively good reproducibility and provide prognostic information on patients with heart disease. Linear time and frequency domain measures have been most commonly used to quantify the fluctuation in heart rate around its mean value, but there is increasing evidence to suggest that the heart is not a periodic oscillator under normal physiologic conditions, and commonly used moment statistics of HRV are not able to describe accurately changes in beat to beat heart rate dynamics. Therefore, nonlinear methods have been developed to quantify the dynamics of heart rate fluctuations.

Nonlinear means of assessing heart rate and its dynamics may provide additional information regarding cardiac autonomic fluctuations that cannot be detected by linear-based methods, such as HRV, alone. Both branches of the autonomic nervous system (ANS) contribute to nonlinear oscillations in heart rate kinetics. Complexity refers to the irregularity of a dynamic process and can be measured quantitatively by assessment of the uncertainty of patterns reoccurring within a time-event series. Complexity and variability are not necessarily analogous terms: a periodic sinusoidal signal can be variable but not complex, whereas a random signal may be less variable and highly complex. Reduction in heart rate complexity occurs with aging and cardiovascular diseases, such as myocardial infarction and congestive heart failure, and is independently associated with mortality after myocardial infarction. Reductions in heart rate complexity have also been shown to predict onset of paroxysmal atrial fibrillation and can occur despite no change in traditional HRV parameters. Thus, nonlinear methods of beat-to-beat heart rate assessment provide complementary and additive information beyond traditional spectral measures of HRV. Thus, HRC may non-invasively foretell the capabilities of an athlete, for example, by correlating higher HRC, measured by nonlinear means, to athletic performance.

Turning now to FIG. 1, a system 100 for assessment of cardiovascular fitness, for example, is shown. The system 100 includes a network 102, such as a Transport Control Protocol/Internet Protocol (TCP/IP) network (e.g., the Internet or an intranet). A local monitoring device 104 may be operably coupled to the network 102, and a remote monitoring system 106 may also be operably coupled to the network 102. The remote monitoring system 106 may include a desktop computer, a laptop computer, a hand held computer, a cellular phone, a wireless phone, a wireless handheld device, an Internet access device, and the like. A subject 108, such as an athlete, may be coupled to the local monitoring device 104, which may be a cardiac monitor, for example, including one or more sensors to acquire cardiac information. A database 110, such as a cloud storage system, may also be coupled to the local monitoring device 104 and/or the remote monitoring system 106 through the network 102.

The local monitoring device 104 and, in some embodiments, the remote monitoring system 106, include a respective network interface for communicating with the network 102 (e.g., outputting information to, and receiving information from, the network 102), such as by transferring information (e.g., instructions, data, signals, etc.) between such systems and the network 102. Accordingly, through the network 102, the local monitoring device 104 may communicate with the remote monitoring system 106, and the remote monitoring system 106 may communicate with the local monitoring device 104.

With continued reference to FIG. 1, the remote monitoring system 106 includes a respective processor 111 for executing processes and performing operations (e.g., processing or communicating information) in response thereto. For example, the remote monitoring system 106 may be configured to receive and process input data 112 (e.g., heart rate data) acquired by the local monitoring device 104. The remote monitoring system 106 may further include a display device 114 (e.g., a conventional electronic cathode ray tube (CRT) device or a conventional liquid crystal display (LCD)), which is operably coupled to the processor 111 for displaying information to the subject 108.

The processor 111 may be structurally and functionally interrelated with a respective computer-readable medium such as, for example, a memory, a hard disk drive, a solid state memory device, and/or a variety of other computer-readable media known in the art. The computer-readable medium stores (e.g., encodes, records, or embodies) functional descriptive material (e.g., including but not limited to software or data structures). As such, the processor 111 may perform the operation of processing a computer application (that is stored, encoded, recorded, or embodied on a computer-readable medium) for causing the processor 111 to perform additional operations. In addition to reading such functional descriptive material from the computer-readable medium, the processor 111 may be capable of reading such functional descriptive material from (or through) the network 102.

As discussed above, the remote monitoring system 106 may be configured to receive and process input data 112 acquired by the local monitoring device 104 using an algorithm stored on the computer-readable medium. In one non-limiting example, the input data 112 may include electrocardiogram (EKG) recordings from an EKG device that is coupled to the local monitoring device 104. The EKG recordings may then be processed by the processor 111, for example, of the remote monitoring system 106 to calculate HRC of the subject's 108 heart rate signals using sample entropy (SampEn), as will be described in further detail below. Based on the calculated HRC data, cardiovascular fitness of an athlete, for example, can be predicted. In other embodiments, the calculated HRC data may be used for surgery recovery patients and/or physical therapy patients to predict cardiovascular fitness.

Figure 2:
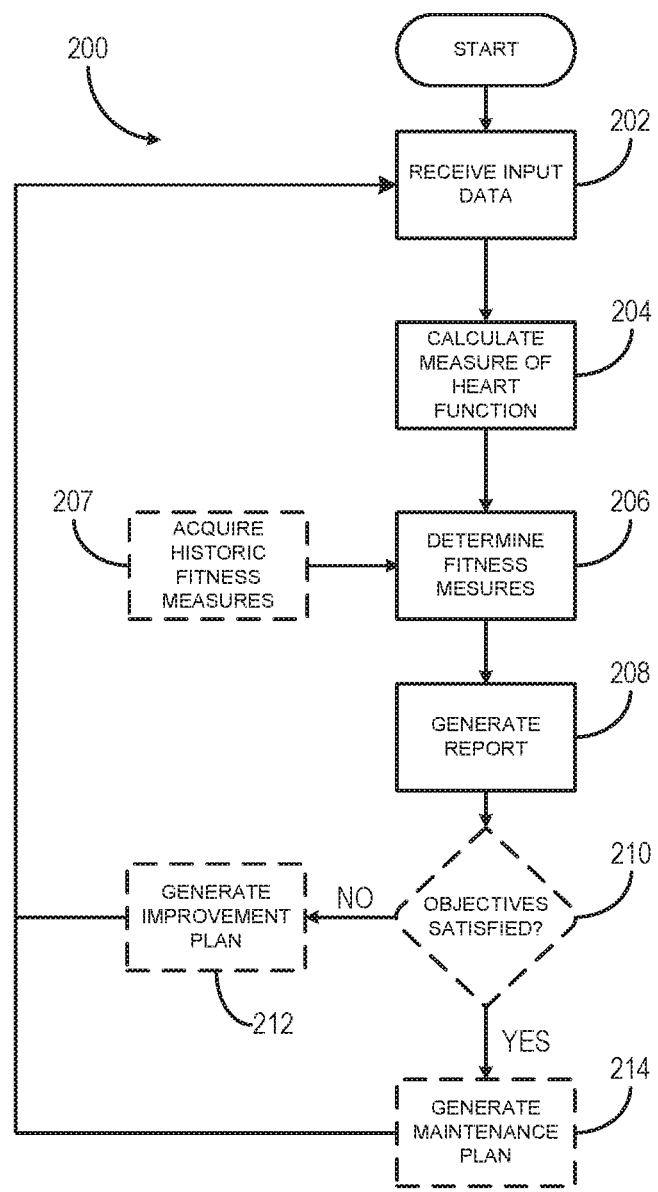
FIG. 2 is a flow chart setting forth the steps of processes for assessing cardiovascular fitness of a subject.

Referring now to FIG. 2, a flow chart setting for exemplary steps 200 for assessing HRC of the subject is provided. To start the process, input data 112 acquired by the local monitoring device 104 may be received by the remote monitoring system 106 at process block 202. In one non-limiting example, the local monitoring device 104 may be a non-invasive cardiac monitor coupled to the subject 108. The local monitoring device 104 may take the form of a chest band, for example, in order to acquire the input data 112 from the subject 108. The local monitoring device 104 may be directly or wirelessly coupled to the remote monitoring system 106, such as a hand-held mobile device also worn by the subject 108. Accordingly, the subject 108 can see HRC data in real-time while performing a physical activity including, but not limited to, running, swimming, walking, biking, or playing any major sport. In other embodiments, the remote monitoring system 106 may be integrated into exercise equipment (e.g., a treadmill, stair climber, etc.), and the remote monitoring system 106 may receive the input data 112 from the local monitoring device 104 coupled to the subject 108. In another embodiment, the remote monitoring system 106 may be in the form of a laptop or desktop computer, for example, that is configured to receive the input data 112 over the network 102 from the local monitoring device 104. As such, the subject 108 can view the input data 112 after performing the physical activity, for example.

With continued reference to FIG. 2, the input data 112 received at process block 202 may include EKG recordings or similar cardiac or heart monitoring information. In one non-limiting example, the input data may include EKG data spanning two-hundred consecutive beats from the subject 108, for example, in a continuous sliding window-fashion. Input data 112 may further include real-time measurements of cardiac output (CO), thoracic impedance, heart rate (HR), stroke volume (SV), and thoracic fluid content (TFC), which is a measure of thoracic fluid volume calculated by noninvasive thoracic impedance cardiography. The other input data 112 may also be obtained by electrical impedance cardiography. In some configurations, left ventricular ejection time (LVET) may also be received as input data 112 at process block 202. LVET is a measure of the time between aortic valve opening and closing. Recent work has found an inverse correlation between LVET and aortic pulse wave velocity, which may be directly related to arterial stiffness. Moreover, endurance trained individuals may have significantly reduced arterial stiffness compared to less active, age-matched controls.

Once the input data 112 is acquired by the local monitoring device 104 and received by the remote monitoring system 106 at process block 202, the processor 111 may calculate a measure of heart functionality over time using the acquired input data at process block 204. In one non-limiting example, the measure of heart functionality may include, for example, HRC and/or HRV data that is calculated by analyzing EKG data over a desired temporal window, such as ten second intervals.

HRC may be calculated using sample entropy (SampEn), which is a technique used to measure the likelihood of finding similar patterns in a continuous signal. More specifically, SampEn may be used to determine a probability of finding specific patterns or matches in a short time series, and typically ranges from 0 to 2. In a highly predictive (i.e., regular) signal, such as a sine wave, SampEn may have a value close to 0. In contrast, a highly irregular signal may have a SampEn value close to 2.

Once the heart functionality is measured at process block 204, the heart functionality information (e.g., HRC) may be used to determine a fitness measure for the individual at process block 206. For example, in the case of the heart rate functionality information being HRC, the HRC may be compared to stored information and/or a threshold value at process block 206 to determine a relative fitness measure. That is, the heart rate functionality information may be compared to a reference dataset that includes correlated information for a range of individuals of different, known fitness levels. The threshold value may be selected based on the individual or objectives for the individual. For example, if the subject is a marathon runner looking to complete an upcoming marathon within a specific time period, the HRC threshold may be higher, for example, than for a runner looking to complete a 5K road race within a specific time period. In addition, different threshold values may be utilized base on, for example, different groups of athletes utilizing the system 100. For example, heart rate data of female runners between the ages of 18-25 may be compared to a different threshold value than heart rate data of male runners between the ages of 26-35, for example. Accordingly, the subject may enter input data, such as age, sex, weight, height, and the like, at process block 202 that may be used by the processor 111 when comparing the heart functionality measurement to determine fitness measures at process block 206. As such, the comparison may be a lookup table or other database of information against which to correlate the heart functionality information at process block 206. Additionally, or alternatively, the subject 108 may enter a specific goal (e.g., a desired finish time) as input data at process block 202 that may be used by the processor 111 when comparing the heart functionality information. To this end, for example, the determination at process block 206 may be made relative to historic fitness measures acquired/stored at process block 207. As will be described, this information may be used in a variety of ways, including to track, demonstrate, and guide a user toward specific fitness goals or performance metrics.

That is, at process block 208, a report may be generated. The report may be displayed on the display 114 of the remote monitoring system 106, for example, and may indicate the subject's heart functionality information and fitness measures. The report may include static indications of the fitness measures or relative fitness of the subject. Additionally or alternatively, the report generated at process block 208 may be used to determine if the heart function information satisfies particular objectives of the individual. As a non-limiting example, a specific goal of the subject may be to finish a marathon or 5K run in less than a particular time. To this end, at decision block 210, the report can be used to determine if the subject's level of physical fitness is capable of achieving the desired fitness objective. For example, in the example of a distance runner, it is well established that the individual does not need to attempt and, in fact likely should not attempt in a distance training exercise, to run the desired distance (e.g., a marathon) at a desired "race pace." As a result, it can be very difficult for an individual to objectively determine whether he or she is in sufficient physical condition to achieve the desired "race pace" in race conditions over the entire distance. Historically, both professional and amateur athletes rely on experience to subjectively guess if the current level of physical fitness is sufficient to achieve the desired results during a race. However, using the systems and methods of the present disclosure, this determination can be made objectively at optional decision block 210 and, furthermore, can be translated into a personalized improvement plan at optional process block 212. That is, not only can the above-described systems and methods provide objective indications of whether an individual has reached a particular level of physical fitness, the systems and methods can be used to provide an individualized plan to improve physical fitness to reach the personal objectives.

The improvement plan may be generated at optional process block 212 by determining a relative variation of the fitness measures from the individual's fitness objectives. To this end, the system may indicate that the subject is not prepared for the marathon run, for example, because a predicted finish time is below a desired finish time provided by the subject. Additionally, the improvement plan may recommend how the subject can improve the desired finish time. For example, the improvement plan may recommend that the subject 108 run a certain distance or run for a certain time period each day in order to improve the subject's cardiovascular fitness level.

On the other hand, once the individual has reached the desired objective at optional decision block 210, a personalized maintenance plan may be provided at optional process block 214. That is, when the system determines that the relative variation of the fitness measures from the individual's fitness objectives is below a threshold value or within a reasonable or predetermined tolerance, a maintenance plan may be generated. The maintenance plan may indicate that the subject is prepared for the marathon run, for example, and predict a finish time. Additionally, the maintenance plan may recommend how the subject can maintain the desired finish time. For example, the maintenance plan may recommend that the subject 108 run a certain distance or run for a certain time period each day in order to maintain the subject's cardiovascular fitness level.

Once the maintenance plan or improvement plan is generated at process blocks 212 and 214, respectively, input data 112 may again be acquired by the local monitoring device 104 and received by the remote monitoring system 106 at process block 202 when the subject 108 begins a subsequent fitness activity, for example. The system 100 may be configured to continuously or regularly receive the input data, update the subject's heart function information, and store the maintenance and/or improvement plans in the database 110 until the subject has reached a desired cardiovascular fitness level or goal. Thus, the subject 108 may access the maintenance and/or improvement plans and corresponding heart functionality data from the remote monitoring system 106 at any time. In an alternative embodiment, the system 100 may be utilized for a single use application.

EXAMPLE

In one non-limiting, experimental example, forty-two marathoners and eighteen self-reported sedentary, but otherwise healthy controls were prospectively enrolled in a case control study. Marathoners were furthermore subdivided into two groups: those whose most recent marathon finish time met the Boston Marathon qualifying standard (BQ, determined by age/sex) and those whose time did not (Non-BQ).

To calculate SampEn, recordings of 200 consecutive beats in a continuous sliding-window fashion were used. For these calculations, the dimension parameter m was 2 and the filter parameter r was 20% of the standard deviation (SD). Measurement of HRV was determined using standard deviation of the normal-to-normal RR interval (SDRR) time-domain analysis. For each subject, both peak and mean HRC was calculated. Peak HRC was defined as the highest recorded complexity over the duration of recording.

Data was reported as means (SD), medians (interquartile range), and frequencies (%), as appropriate. HRC, HRV, and other continuous variables were compared between groups using Student's t test. Correlation data were assessed using Pearson's correlation coefficient. Data were compared between marathoners and controls, as well as between BQ and non-BQ marathoners. A statistical analysis system (SAS) was used for statistical analysis. A $p<0.05$ was considered statistically significant.

Compared to sedentary controls, marathoners demonstrated higher mean HRC (2.15±0.42 vs. 1.79±0.60, p=0.03) and peak HRC (2.78±0.60 vs. 2.18±0.74, p=0.005). Additionally, marathoners had increased TFC (1/mOhm, 33.0±8.4 vs. 23.9±3.9, p<0.0001) and LVET (309.8±19.6 msec vs. 288.7±17.3, p=0.0002). Among marathoners, those meeting the BQ standard had higher mean HRC (2.33±0.43 vs. 2.03±0.38, p=0.027) than those not meeting the BQ standard. Resting heart rate did not significantly differ between these two groups (65.9±10.5 vs. 60.8±7.4, p>0.05). In addition, marathoners had significantly lower HRs than controls (63.8±9.6 vs. 78.3 ±9.8 p<0.0001).

In the marathoner cohort, mean HRC was higher in the BQ group versus Non-BQ (2.33±0.43 vs. 2.03±0.38, p=0.027). Mean HRV was also increased in BQ subjects (69.6±29.3 vs. 50.3±18.2, p=0.023). Resting heart rate between BQ and non-BQ was not statistically different (BQ=60.8±7.4 vs. Non-BQ=65.9±10.5, p=0.07). No significant differences in peak HRC or CO were identified.

To assess whether HRC correlated with most recent finish time over a continuous range of times, deviation time, which reflects how close a runner finished to the standard, was used. Zero is the BQ standard, scaled in minutes. Positive values represent times slower than the standard, while negative values indicates deviation times faster than the BQ standard for a given sex and age. A Pearson product-moment correlation coefficient was calculated to determine the relationship between mean HRC and deviation time. There was a negative correlation between these two variables (r=−0.339, n=42, p<0.05). No correlation was found with HR, HRV, or peak HRC.

Marathoners had a significantly higher LVET than sedentary controls. Longer ejection times may be associated with larger blood volumes, and correspondingly, greater SV, as well as lower peripheral vascular resistance and increased venous return in athletes. Further, marathoners had significantly higher TFC than controls. A 1 kohm$^{-1}$ change in TFC represents a ~200 mL change in total body water. Thus, total fluid volume in marathoners was approximately 1.8 L more than in controls. This may result from increased hydration or cardiovascular compensatory mechanisms in athletes.

SDNN measurement among marathoners showed that BQ runners had higher HRV than non-BQ runners. Marathoners as a whole had non-significantly higher HRV compared to controls. However, those runners who did not meet the BQ standard actually showed similar HRV to controls (50.3±18.2 vs. 47.9±25.2). In one example, in swimmers and runners who train at higher intensities or overtrain, HRV decreases by up to 38%. Even in elite athletes, HRV decreases after overtraining. Accordingly, the relationship between HRV and training load tends to be a bell shaped curve, where a certain intensity of training can maximize HRV. Training at intensities higher or lower than this peak decreases variability.

In conclusion, in otherwise healthy volunteers, both mean and peak HRC are indicators of cardiovascular fitness. Moreover, HRC successfully discriminated elite BQ marathoners from non-BQ marathoners, as well as sedentary controls. Thus, HRC represents a new and useful vital sign for evaluating and tracking cardiovascular fitness. Specifically, this study demonstrates that Boston qualified marathon runners have higher HRC (by SampEn) than non-Boston qualified runners. In addition, elite marathoners have higher mean HRC and HRV than sub-elite marathoners, increased HRC is correlated with faster finish times relative to the BQ standards, and marathoners exhibit longer LVET and higher TFC than sedentary controls.

The present invention has been described in terms of one or more preferred embodiments, and it should be appreciated that many equivalents, alternatives, variations, and modifications, aside from those expressly stated, are possible and within the scope of the invention.

The invention claimed is:

1. A system for tracking athletic fitness of an individual, the system comprising:
    a sensor configured to be coupled to the individual to acquire cardiac information about the cardiac performance of the individual over time, the sensor comprising an electrocardiogram (EKG) device configured to acquire the cardiac information by generating EKG data for the individual;
    a processor configured to receive the cardiac information from the sensor and configured to:
        determine, from the cardiac information, heart function data that include heart rate complexity (HRC) data and heart rate variability (HRV) data;
        compare the heart function data for the individual to at least one predetermined threshold value and to a reference dataset that includes correlated information for a range of individuals of different, known fitness levels to determine a measure of fitness of the individual;
        generate a maintenance plan when the HRC data is above the at least one predetermined threshold value, the maintenance plan including recommendations for maintaining a cardiovascular fitness level of the individual; and
        generate an improvement plan when the HRC data is below the at least one predetermined threshold value, the improvement plan including recommendations for improving the cardiovascular fitness level of the individual; and
    a display coupled to the processor and configured to display the measure of fitness for the individual.

2. The system of claim 1 wherein the processor is further configured to receive an indication of a fitness objective for the individual and to determine a relative variation of the measure of fitness for the individual from the fitness objective.

3. The system of claim 2 wherein the display is further configured to display a report indicating the relative variation.

4. The system of claim 2 wherein the improvement plan includes recommendations to reduce the relative variation.

5. A system for assessing cardiovascular fitness of a subject, the system comprising:
    a local monitoring device coupled to the subject for acquiring input data related to the subject, the local monitoring device comprising an electrocardiogram (EKG) device, and the input data comprising EKG data for the subject;
    a remote monitoring system communicatively coupled to the local monitoring device for receiving the input data, the remote monitoring system including a non-transitory memory having stored thereon an algorithm to be applied to the input data;
    a processor having access to the non-transitory memory and the algorithm stored thereon and configured to:
        calculate heart rate complexity (HRC) data and heart rate variability (HRV) data based on the input data, compare the HRC data to at least one predetermined threshold value, process the HRC data in relation to the at least one predetermined threshold value to generate a cardiovascular fitness level of the subject, generate a maintenance plan when the HRC data is above the at least one predetermined threshold value, the maintenance plan including recommendations for maintaining the cardiovascular fitness level of the subject, and generate an improvement plan when the HRC data is below the at least one predetermined threshold value, the improvement plan including recommendations for improving the cardiovascular fitness level of the individual; and a display coupled to the remote monitoring system and configured to display a report related to the cardiovascular fitness level of the subject.

6. The system as recited in claim 5 wherein the remote monitoring system includes at least one of a desktop computer, a laptop computer, a hand held computer, a cellular phone, a wireless phone, a wireless handheld device, or Internet access device.

7. The system as recited in claim 5 wherein the input data further includes at least one of age, sex, weight, height, or a fitness goal related to the subject.

8. The system as recited in claim 7 wherein the at least one predetermined threshold value is determined based upon at least one additional subject having similar input data.

9. The system as recited in claim 5 wherein the HRC data is calculated by processing the EKG data using sample entropy.

10. A method for assessing cardiovascular fitness of a subject, the method comprising the steps of:

receiving, by a processor, from a local monitoring device coupled to the subject, input data related to the subject, the local monitoring device comprising an electrocardiogram (EKG) device, and the input data comprising EKG data for the subject;

calculating, by the processor, heart rate complexity (HRC) data and heart rate variability (HRV) data based on the received EKG data using an algorithm applied to the EKG data;

comparing, by the processor, the HRC data to at least one predetermined threshold value and processing the HRC data in relation to the at least one predetermined threshold value to generate a cardiovascular fitness level of the subject;

generating, by the processor, a maintenance plan when the HRC data is above the at least one predetermined threshold value, the maintenance plan including recommendations for maintaining the cardiovascular fitness level of the subject, and generating, by the processor, an improvement plan when the HRC data is below the at least one predetermined threshold value, the improvement plan including recommendations for improving the cardiovascular fitness level of the individual; and generating and displaying, by the processor, a report related to the cardiovascular fitness level of the subject on a display communicatively coupled to the local monitoring device.

11. The method as recited in claim 10 wherein the remote monitoring system includes at least one of a desktop computer, a laptop computer, a hand held computer, a cellular phone, a wireless phone, a wireless handheld device, or Internet access device.

12. The method as recited in claim 10 wherein the input data further includes at least one of age, sex, weight, height, or a fitness goal related to the subject.

13. The method as recited in claim 12 wherein the at least one predetermined threshold value is determined based upon at least one additional subject having similar input data.

14. The method as recited in claim 10 wherein calculating the HRC data includes processing the EKG data using sample entropy.

* * * * *